(12) United States Patent
Larkin et al.

(10) Patent No.: US 8,246,028 B2
(45) Date of Patent: Aug. 21, 2012

(54) TELESCOPINGLY ADJUSTABLE CLAMP

(75) Inventors: Harold Larkin, Three Mile Bay, NY (US); Jeffrey Gibson, Richville, NY (US); Kirk Aubertine, Three Mile Bay, NY (US)

(73) Assignee: Tyco Healthcare Group LP, Mansfield, MA (US)

( * ) Notice: Subject to any disclaimer, the term of this patent is extended or adjusted under 35 U.S.C. 154(b) by 1321 days.

(21) Appl. No.: 11/937,176

(22) Filed: Nov. 8, 2007

(65) Prior Publication Data
US 2009/0125055 A1    May 14, 2009

(51) Int. Cl.
*B25B 1/20* (2006.01)
*B25B 13/22* (2006.01)
*B23Q 3/02* (2006.01)
*G09F 7/18* (2006.01)
*A61B 17/12* (2006.01)

(52) U.S. Cl. ......... 269/249; 269/43; 269/96; 248/229.1; 81/139

(58) Field of Classification Search .................. 269/249, 269/43, 45, 96, 97; 248/229.1, 229.25; 403/321, 403/322.3; 81/139
See application file for complete search history.

(56) References Cited

U.S. PATENT DOCUMENTS

| | | | | |
|---|---|---|---|---|
| 742,055 A * | 10/1903 | Ondrey | ........................... | 81/143 |
| 762,762 A * | 6/1904 | Rowe | ............................. | 81/145 |
| 878,394 A | 2/1908 | Holle | | |
| 910,737 A * | 1/1909 | Stenz | ............................. | 81/143 |
| 991,602 A * | 5/1911 | Bradley | ............................ | 81/97 |
| 994,070 A * | 5/1911 | Fieldes | ............................ | 81/139 |
| 1,064,361 A * | 6/1913 | Moak | ............................. | 81/140 |
| 1,181,380 A * | 5/1916 | Gorder | ........................... | 81/139 |
| 1,199,806 A * | 10/1916 | Merritt | ........................... | 81/145 |
| 1,289,937 A * | 12/1918 | Shade | ............................. | 81/145 |
| 1,377,930 A * | 5/1921 | Roach | ............................ | 81/137 |
| 1,612,659 A * | 12/1926 | Spangler | ........................ | 81/92 |
| 1,643,002 A * | 9/1927 | Beszczak | ........................ | 81/134 |
| 1,999,225 A * | 4/1935 | Williamson | ................. | 105/26.1 |
| 2,033,491 A | 3/1936 | Sprague et al. | | |
| 2,607,881 A | 8/1952 | Anderson | | |

(Continued)

FOREIGN PATENT DOCUMENTS
DE       4208128 A1    9/1992
(Continued)

OTHER PUBLICATIONS

European Search Report regarding related application serial No. EP 08168629.7 dated Sep. 6, 2011—8 pgs.

*Primary Examiner* — Lee D Wilson
*Assistant Examiner* — Alvin Grant
(74) *Attorney, Agent, or Firm* — Thomas M. Johnston, Esq.

(57) ABSTRACT

A telescopingly adjustable clamp for securing an object to a support may include an anchor rod with a plurality of circumferentially extending grooves which define at least one barrier wall. A positioning member defines a receptacle that receives a portion of the anchor rod and allows motion of the anchor rod relative to the positioning member in the receptacle. The positioning member includes a positioning tab that projects into the receptacle and is sized and shaped to be received in one of the grooves. The positioning member supports a clamping member that extends generally radially outwardly from the longitudinal axis of the anchor rod. Relative movement of the anchor rod and the positioning member changes the distance between the clamping member and the object.

13 Claims, 11 Drawing Sheets

U.S. PATENT DOCUMENTS

| | | | |
|---|---|---|---|
| 2,945,946 A | | 7/1960 | Moffatt |
| 3,030,639 A | | 4/1962 | Boyer |
| 3,039,338 A | * | 6/1962 | Borg .................. 81/134 |
| 3,075,723 A | | 1/1963 | Wohlfeil |
| 3,757,363 A | | 9/1973 | Langlais |
| 4,101,089 A | | 7/1978 | Culbertson et al. |
| 4,262,872 A | | 4/1981 | Kodet |
| 4,443,128 A | | 4/1984 | Yamamoto et al. |
| 4,444,548 A | | 4/1984 | Andersen et al. |
| 4,487,523 A | * | 12/1984 | Monroe .................. 403/385 |
| 4,547,092 A | | 10/1985 | Vetter et al. |
| 4,576,501 A | * | 3/1986 | McConnell .................. 403/59 |
| 4,593,422 A | * | 6/1986 | Wolpert et al. .............. 5/503.1 |
| 4,627,604 A | * | 12/1986 | Choi .................. 269/214 |
| 4,676,687 A | | 6/1987 | Koffler |
| 4,695,025 A | | 9/1987 | Vaughan |
| 4,699,344 A | | 10/1987 | Vaughan |
| 4,702,448 A | * | 10/1987 | LoJacono et al. .......... 248/227.3 |
| 4,742,981 A | * | 5/1988 | Converse .................. 248/231.71 |
| 4,796,846 A | | 1/1989 | Meier et al. |
| 4,865,484 A | * | 9/1989 | McConnell .................. 403/59 |
| 4,872,224 A | | 10/1989 | Grimes et al. |
| 4,885,667 A | | 12/1989 | Selden |
| 4,903,922 A | | 2/1990 | Harris, III |
| 4,970,900 A | | 11/1990 | Shepherd et al. |
| 4,988,062 A | | 1/1991 | London |
| 5,025,780 A | | 6/1991 | Farley |
| 5,033,337 A | * | 7/1991 | Thomas, III .................. 81/177.2 |
| 5,108,213 A | | 4/1992 | Shields |
| 5,118,127 A | | 6/1992 | Partington |
| 5,163,752 A | | 11/1992 | Copeland et al. |
| 5,230,264 A | * | 7/1993 | Kindling .................. 81/151 |
| 5,242,240 A | | 9/1993 | Gorham |
| 5,275,390 A | * | 1/1994 | Brennan .................. 269/68 |
| 5,320,444 A | | 6/1994 | Bookwalter et al. |
| 5,334,186 A | | 8/1994 | Alexander |
| 5,340,069 A | * | 8/1994 | Niemeyer .................. 248/214 |
| 5,368,267 A | | 11/1994 | Howard |
| 5,540,561 A | | 7/1996 | Johnson |
| 5,582,379 A | | 12/1996 | Keselman et al. |
| 5,588,166 A | | 12/1996 | Burnett |
| 5,615,682 A | | 4/1997 | Stratz, Sr. |
| 5,624,403 A | | 4/1997 | Jaquith |
| 5,664,750 A | * | 9/1997 | Cohen .................. 248/231.71 |
| 5,673,888 A | * | 10/1997 | Garguilo .................. 248/228.3 |
| 5,704,577 A | * | 1/1998 | Gordon .................. 248/229.2 |
| 5,733,061 A | | 3/1998 | Child |
| 5,738,319 A | | 4/1998 | Grassi |
| 5,782,611 A | | 7/1998 | Neftel et al. |
| 5,806,814 A | | 9/1998 | White |
| 5,807,333 A | | 9/1998 | Osborne et al. |
| 5,845,664 A | * | 12/1998 | Ryder et al. .................. 135/65 |
| 5,868,710 A | | 2/1999 | Battiato et al. |
| 5,873,386 A | | 2/1999 | Arosio |
| 5,873,555 A | | 2/1999 | Crace |
| D407,010 S | | 3/1999 | Sobczynski |
| 5,876,359 A | | 3/1999 | Bock et al. |
| 5,937,950 A | | 8/1999 | Adams et al. |
| 5,940,904 A | | 8/1999 | Lutz |
| 6,079,678 A | | 6/2000 | Schott et al. |
| 6,085,766 A | * | 7/2000 | Geary .................. 135/75 |
| 6,202,266 B1 | * | 3/2001 | Van den Branden et al. ... 24/569 |
| 6,340,154 B1 | * | 1/2002 | Young .................. 269/246 |
| 6,450,436 B1 | | 9/2002 | Tsuji et al. |
| 6,468,237 B1 | | 10/2002 | Lina |
| 6,497,539 B2 | * | 12/2002 | Marroncelli .................. 409/146 |
| 6,536,699 B2 | | 3/2003 | Glass |
| 6,676,678 B2 | * | 1/2004 | Gifford et al. .................. 606/184 |
| 6,688,569 B1 | * | 2/2004 | Weiss .................. 248/229.15 |
| 6,690,280 B2 | | 2/2004 | Citrenbaum et al. |
| 6,695,857 B2 | * | 2/2004 | Gifford et al. .................. 606/153 |
| 6,708,966 B1 | * | 3/2004 | Troudt .................. 269/249 |
| 6,766,674 B2 | * | 7/2004 | Simon .................. 70/202 |
| 6,942,647 B2 | | 9/2005 | Nickels |
| 6,959,572 B2 | * | 11/2005 | Lawrence et al. ............. 72/31.03 |
| 7,108,544 B2 | | 9/2006 | Zoller |
| 7,140,572 B2 | | 11/2006 | Glass |
| 7,160,087 B2 | | 1/2007 | Fathallah et al. |
| 7,178,777 B1 | * | 2/2007 | Banker .................. 248/316.7 |
| 7,393,057 B2 | * | 7/2008 | Fraser .................. 297/392 |
| 7,621,009 B2 | | 11/2009 | Elhabashy |
| 7,731,138 B2 | * | 6/2010 | Wiesner et al. .............. 248/160 |
| 7,909,314 B2 | * | 3/2011 | Roesch et al. .................. 269/6 |
| 2001/0017340 A1 | | 8/2001 | Cernosek et al. |
| 2002/0096608 A1 | | 7/2002 | Cedarberg, III |
| 2003/0019038 A1 | | 1/2003 | Welling et al. |
| 2003/0070236 A1 | | 4/2003 | Barker |
| 2004/0168489 A1 | * | 9/2004 | Simon et al. .................. 70/202 |
| 2004/0195484 A1 | | 10/2004 | Sheeran |
| 2005/0006542 A1 | | 1/2005 | Henning et al. |
| 2005/0077436 A1 | | 4/2005 | Nelson |
| 2005/0087660 A1 | | 4/2005 | Want et al. |
| 2005/0279902 A1 | | 12/2005 | Richter |
| 2006/0278785 A1 | | 12/2006 | Wiesner et al. |
| 2008/0116157 A1 | | 5/2008 | Fulbrook et al. |
| 2008/0272254 A1 | | 11/2008 | Harr et al. |
| 2009/0125055 A1 | * | 5/2009 | Larkin et al. .................. 606/201 |
| 2009/0314923 A1 | * | 12/2009 | Timoszyk et al. ............. 248/647 |

FOREIGN PATENT DOCUMENTS

| | | |
|---|---|---|
| DE | 4238955 A1 | 7/1994 |
| DE | 29708363 U1 | 7/1997 |
| DE | 29810893 U1 | 10/1998 |
| DE | 10012980 A1 | 9/2001 |
| DE | 20206765 U1 | 7/2002 |
| DE | 202006012945 U1 | 11/2006 |
| EP | 0167345 A1 | 1/1986 |
| FR | 2664807 A1 | 1/1992 |
| GB | 2385628 A | 8/2003 |
| WO | 9952487 | 10/1999 |
| WO | 2005082314 A1 | 9/2005 |
| WO | 2006085119 A1 | 8/2006 |

* cited by examiner

TELESCOPINGLY ADJUSTABLE CLAMP

TECHNICAL FIELD

This invention relates to an apparatus for securing an object to a support, particularly for securing a controller of a sequential compression device to a support.

BACKGROUND OF THE INVENTION

Compression of a body part, such as a leg is beneficial to persons who have blood circulation problems, specifically poor venous return to the heart. Compression therapy devices on the market today use one or more pneumatic bladders that encircle the legs and/or feet to apply cyclic compression. The bladders are inflated in a predetermined order, to prescribed pressures and for predetermined time intervals. A controller that operates the inflation normally employs an air pump and valves that operate to direct flow of the air to the bladders. The controller is located remotely from the bladders, such as on the footboard of a bed, on the floor or on a night stand. A bed-hook is attached to the controller for securing the controller to a footboard.

One previous bed-hook design includes a roughly U-shaped rod that is attached at both ends to the rear of the controller. The rod extends outward and is bent downward from the rear of the controller forming a hook. The top of the footboard can be positioned between the controller and the downwardly bent portion of the rod. Because footboards can vary in width and because the looped rod is rigid and can not be adjusted, the controller may not always be securely fixed to the footboard. Another bed-hook design includes two arms which are pivotally attached to the controller. To secure the controller to the footboard of a bed, the arms are swung outwardly from the controller and the footboard is positioned in the space between the arms and the controller.

Previous bed-hook designs do not allow the controller to be securely fixed to footboards having a variety of widths. In some environments the controller must be located on the floor as it can not be safely secured to the bed. Accordingly, a need exists for bed-hooks which are adjustable such that they can be securely fixed to supports with a variety of widths.

SUMMARY OF THE INVENTION

In one aspect, a telescopingly adjustable clamp for securing an object to a support generally comprises an anchor rod having a first end portion, a second end portion and a longitudinal axis. The anchor rod is adapted for affixation to the object at the first end portion of the anchor rod and includes a plurality of axially spaced, circumferentially extending grooves formed in the anchor rod. The grooves define at least one barrier wall between adjacent grooves. The clamp includes a positioning member that defines a receptacle sized and shaped to receive at least the second end portion of the anchor rod and allows motion of the anchor rod relative to the positioning member in the receptacle. The positioning member comprises a positioning tab that projects into the receptacle and is sized and shaped to be received in one of the grooves and retained in said one groove by the barrier wall. At least one of the positioning tab and the barrier wall is resiliently deflectable upon application of a release force along the longitudinal axis of the anchor rod for moving the positioning tab out of one of the grooves. The clamp includes a clamping member supported by the positioning member that extends generally radially outwardly from the longitudinal axis of the anchor rod. Relative movement of the anchor rod and the positioning member changes the distance between the clamping member and the first end portion of the anchor rod for clamping the object to the support.

In another aspect, a clamp for securing an object to a support generally comprises a pair of anchor rods each having a longitudinal axis and is adapted for affixation to the object. The clamp includes positioning members each receiving a respective one of the anchor rods in sliding relation with the positioning member and clamping members each connected to a respective one of the positioning members for conjoint movement with the positioning members relative to the anchor rods. The clamping members extend generally radially outwardly from the longitudinal axes of the anchor rods. The clamp includes a grip member connected to the positioning members and the clamping members that spaces the positioning members. The grip member is sized for being gripped in the hand and has a curved contour.

Other features will be in part apparent and in part pointed out hereinafter. Various refinements exist of the features noted in relation to the above-mentioned aspects of the present invention. Further features may also be incorporated in the above-mentioned aspects of the present invention as well. These refinements and additional features may exist individually or in any combination. For instance, various features discussed below in relation to any of the illustrated embodiments of the present invention may be incorporated into any of the above-described aspects of the present invention, alone or in any combination.

BRIEF DESCRIPTION OF THE DRAWINGS

Corresponding reference characters indicate corresponding parts throughout the drawings.

DETAILED DESCRIPTION OF THE DRAWINGS

Figure 1:
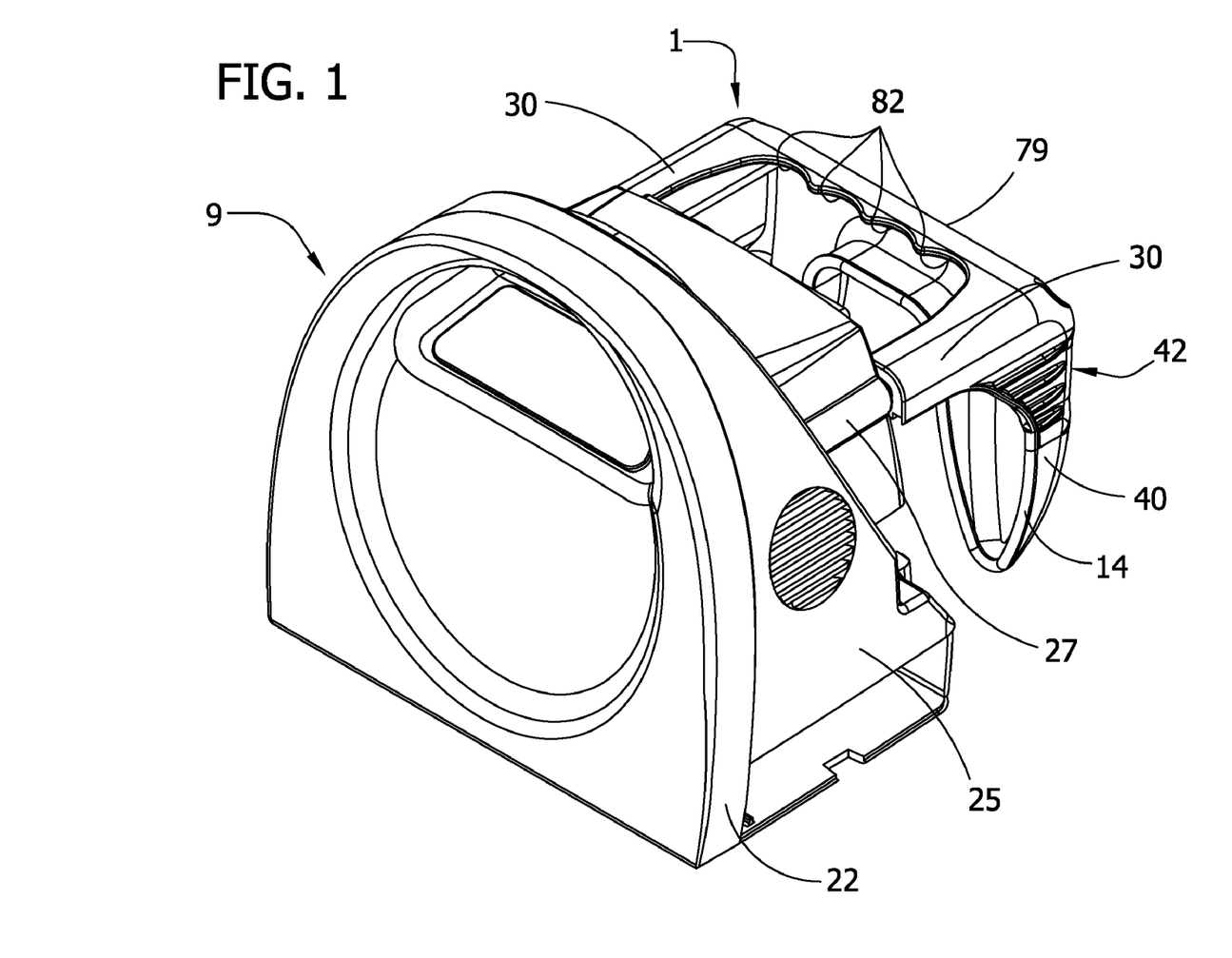
FIG. 1 is a perspective of a clamp and a controller of a sequential compression device.
Figure 2:
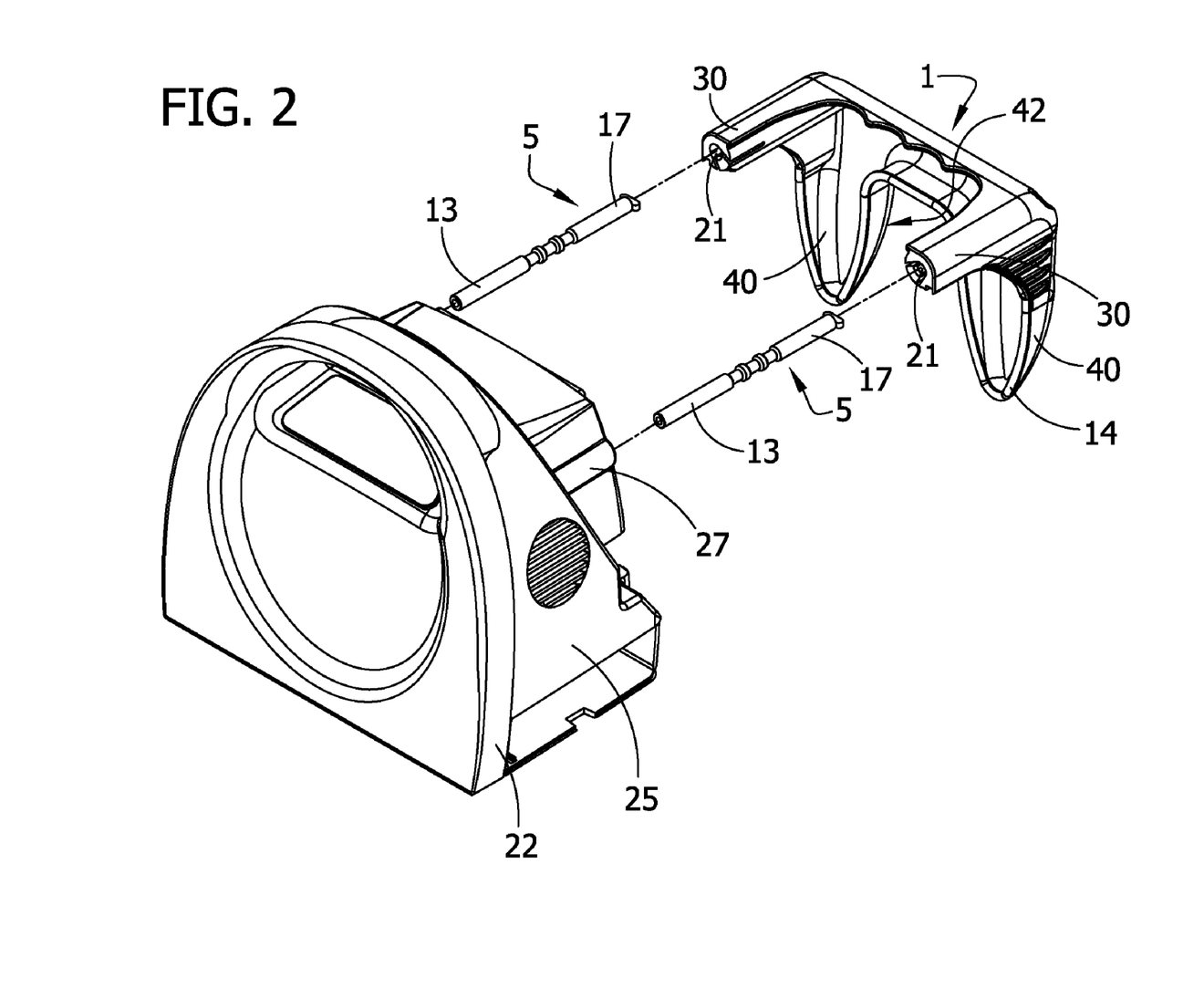
FIG. 2 is an exploded perspective of the clamp and controller of FIG. 1.

Referring now to the drawings, and in particular FIGS. 1, and 2, a clamp constructed according to the principles of the present invention is generally indicated at 1. The clamp 1 is suitable for securing an object to a support and is particularly well-suited for securing a controller 9 of a sequential compression device to, for example, a footboard, headboard or siderail of a medical bed. While the clamp herein is shown as supporting a controller of a sequential compression device, it will be appreciated that the clamp is capable of securing a variety of objects including, for example, various other medical apparatus or non-medical apparatus.

An example of a controller of a sequential compression device and the use of such controller with the device is shown and described in U.S. Pat. No. 5,876,359, the disclosure of which is incorporated herein by reference. The controller 9 includes a faceplate 22 and main body 25. The controller 9 is shown with the clamp 1 exploded therefrom in FIG. 2.

Figure 4:
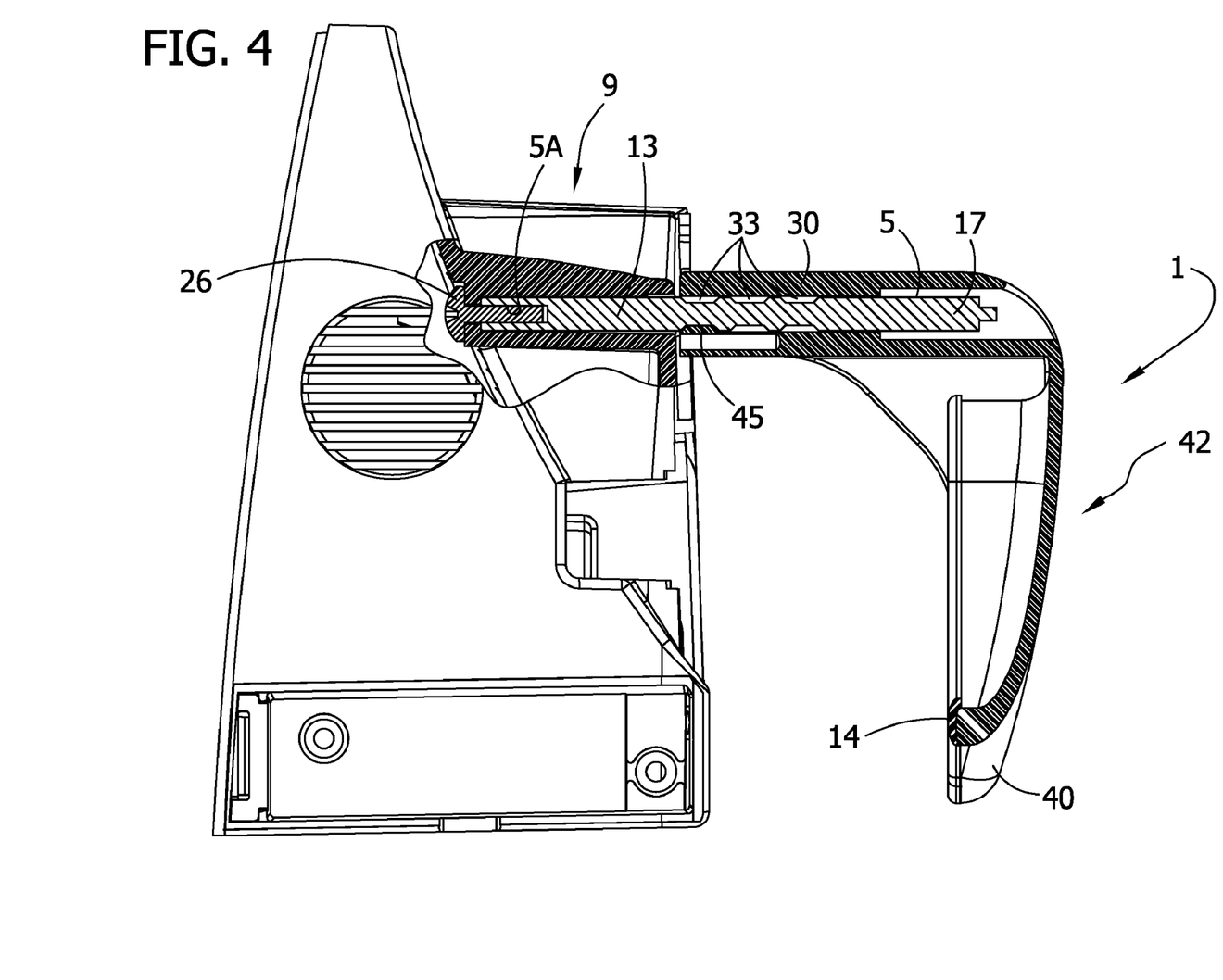
FIG. 4 is a partial section of the clamp and controller with the clamp in a position nearest the controller.

The new clamp 1 is telescopingly adjustable such that the controller can be securely fixed to supports having a variety of widths. Referring to FIG. 1, the clamp includes a pair of anchor rods 5, each defining a longitudinal axis. The number of anchor rods may be greater or fewer than two within the scope of the present invention. Each anchor rod 5 has a first end portion 13 that is adapted to be affixed to the main body 25 of the controller 9. The first end portion 13 of each rod 5 may be affixed by, for example, adhesive, a bolt and nut, or a screw. In the illustrated embodiment each anchor rod 5 is secured to the main body 25 by a bolt 26 received in a threaded opening 5a of the anchor rod (FIG. 4). Alternatively, the first end portion 13 or entire anchor rod 5 may be integral with the controller body 25. Each anchor rod 5 includes a second end portion 17. The anchor rod 5 may be constructed of metal and, preferably, stainless steel.

The clamp 1 includes a pair of positioning members shown generally at 30. Each positioning member 30 defines a receptacle 21. The receptacle 21 is sized and shaped to receive the second end portion 17 of one anchor rod 5. The second end portion 17 of the anchor rod 5 is not affixed to the positioning member 30 but, rather, is capable of movement relative to the positioning member in the receptacle 21.

The positioning members 30 support a clamping member 42. The clamping member 42 extends generally radially outwardly from the longitudinal axis of each respective anchor rod 5. The positioning member 30 may be affixed to the clamping member by, for example, adhesive, nut and bolts, screws, and tongue and groove. In the illustrated embodiment, the positioning member 30 and clamping member 42 are molded as one piece. The clamping member 42 includes a pair of spaced apart legs 40 that project generally radially from the longitudinal axis of the anchor rods 5. Optionally, each leg 40 may include a strip of frictionalizing material, for example rubber, to assist in gripping the support. As shown in the illustrated embodiment, a strip of rubber 14 is located on the back edges of the legs 40. As illustrated, the strip 14 extends continuously from one leg 40 to the other. It will be understood that other configurations with respect to the strip are within the scope of the present invention, such as plural, spaced apart strips. The positioning member 30 and legs 40 may be molded of plastic and, optionally, a resin that is chemically compatible with disinfectants and cleansers used in a hospital setting such as, for example, XENOY, a blend of semi-crystalline polyester and polycarbonate commercially available from GE Plastics (Pittsfield, Mass.).

Figure 3:
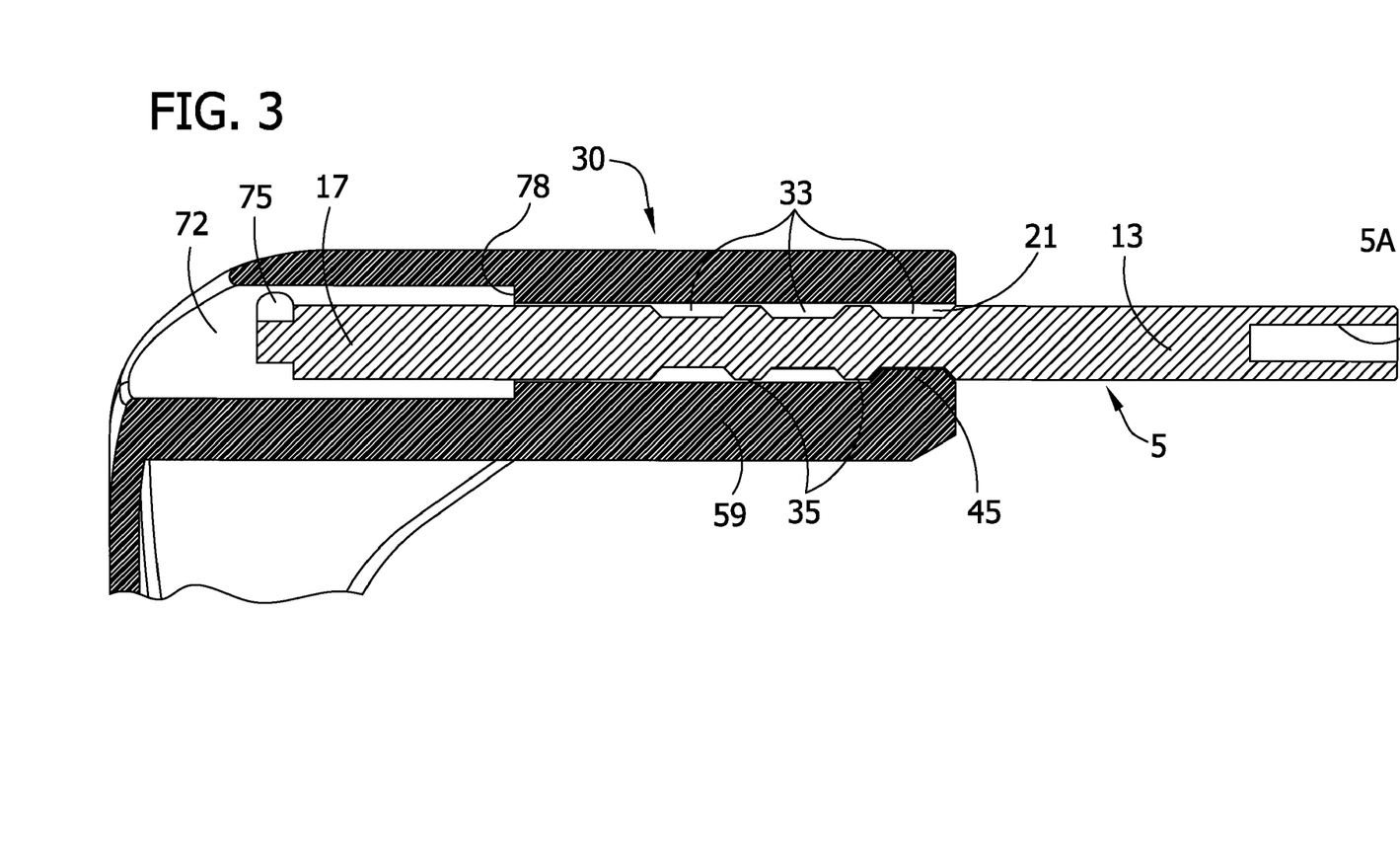
FIG. 3 is an enlarged fragmentary section of the clamp.

Referring now to FIG. 3, a plurality of axially spaced circumferentially extending grooves 33 are formed within the anchor rod 5. The grooves 33 define a pair of barrier walls 35 that separate the grooves. Each positioning member 30 includes a positioning tab 45 sized and shaped to fit within the respective circumferential grooves 33 and to be retained in a groove (at least in part) by the barrier wall 35. As described more fully hereinafter, the positioning tab 45 may be resiliently deflectable so that upon application of a sufficient force along the longitudinal axis of the anchor rod 5 the positioning tab moves out of its groove 33 and relocates in another groove thereby creating a change in distance between the controller 9 and the legs 40 of the clamping member 42. While the clamp is shown with a pair of positioning tabs 45, only one tab is required for the clamp to properly extend and retract. The grooves 33 may be formed within the anchor rod 5 during casting of the anchor rod or may be formed later by machining.

In another embodiment (not shown), the barrier walls 35 of the anchor rod 5 are deflectable rather than the positioning tab 35.

The receptacle 21 defined by the positioning member 30 includes a support section 59 for sliding but close contacting engagement with the anchor rod 5 on both sides of at least one of the grooves 33. The receptacle 21 also includes a capture section 72 for capturing the second end portion 13 of the anchor rod 5. The diameter of the receptacle 21 in the support section 59 is smaller than the diameter of the receptacle in the capture section 72. As a result, a shoulder or stop 78 (FIG. 3) is defined between the support section 59 and the capture section 72. The second end portion 17 includes a retainer 75 that projects outwardly from the anchor rod 5 to a radius larger than the receptacle in the support section 59. The stop 78 limits the retainer 75 to the capture section 72 of the receptacle 21 and prevents the anchor rod 5 from decoupling from the positioning member 30.

Figure 5:
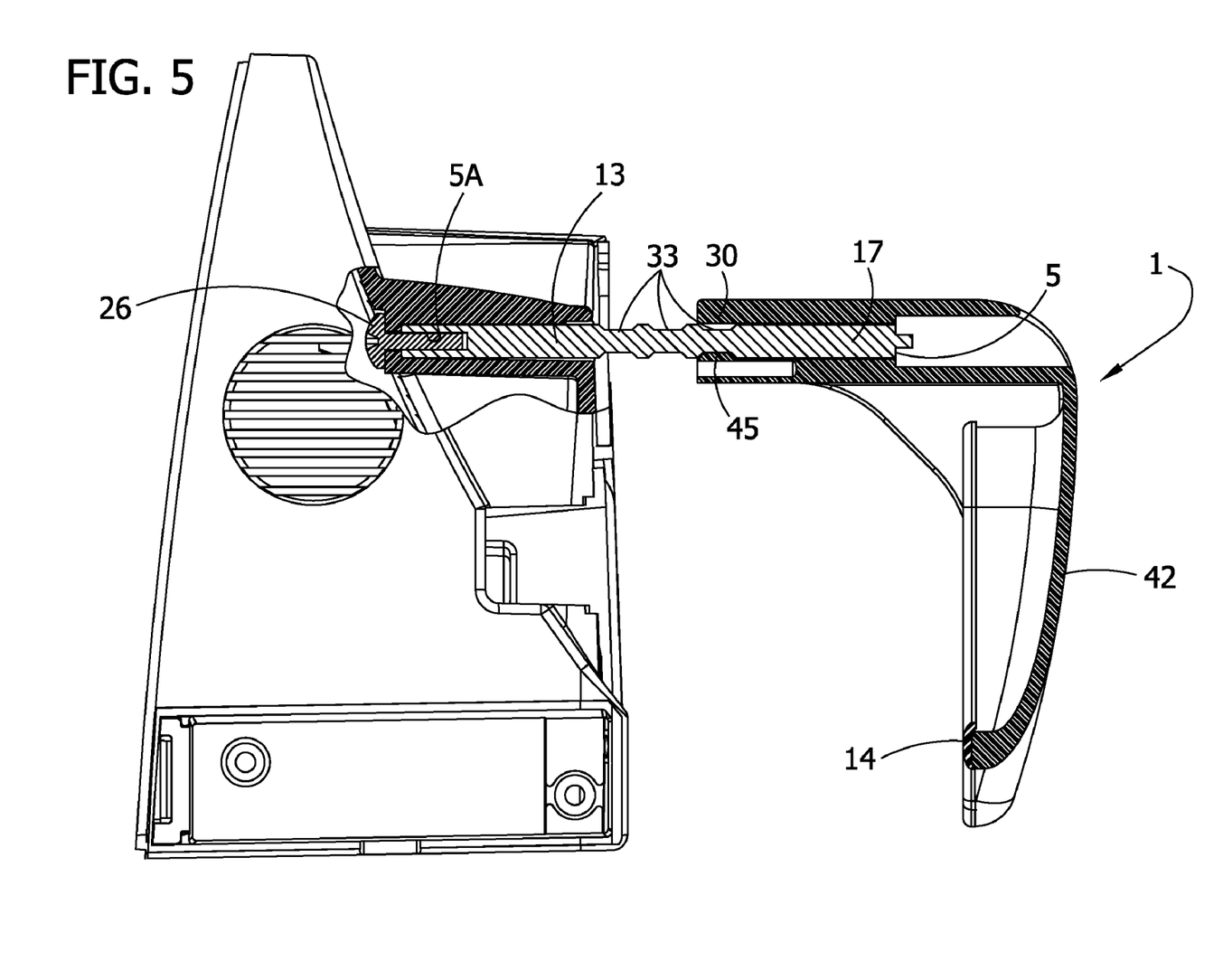
FIG. 5 is the section of FIG. 4, but with the clamp in a position farthest the controller.

Referring to FIG. 4, the clamp 1 is shown in its fully retracted position, i.e., the position with minimum distance between the legs 40 of the clamping member 42 and the controller 9. The clamp 1 is shown in its fully extended position in FIG. 5, i.e., the position with maximum distance between the clamping member 42 and the controller 9. Stated another way, relative movement between the anchor rod 5 and the positioning member 30 changes the distance between the legs 40 of the clamping member 42 and the first end portion 13 of the anchor rod to accommodate footboards or other support structure of various widths.

Figure 6:
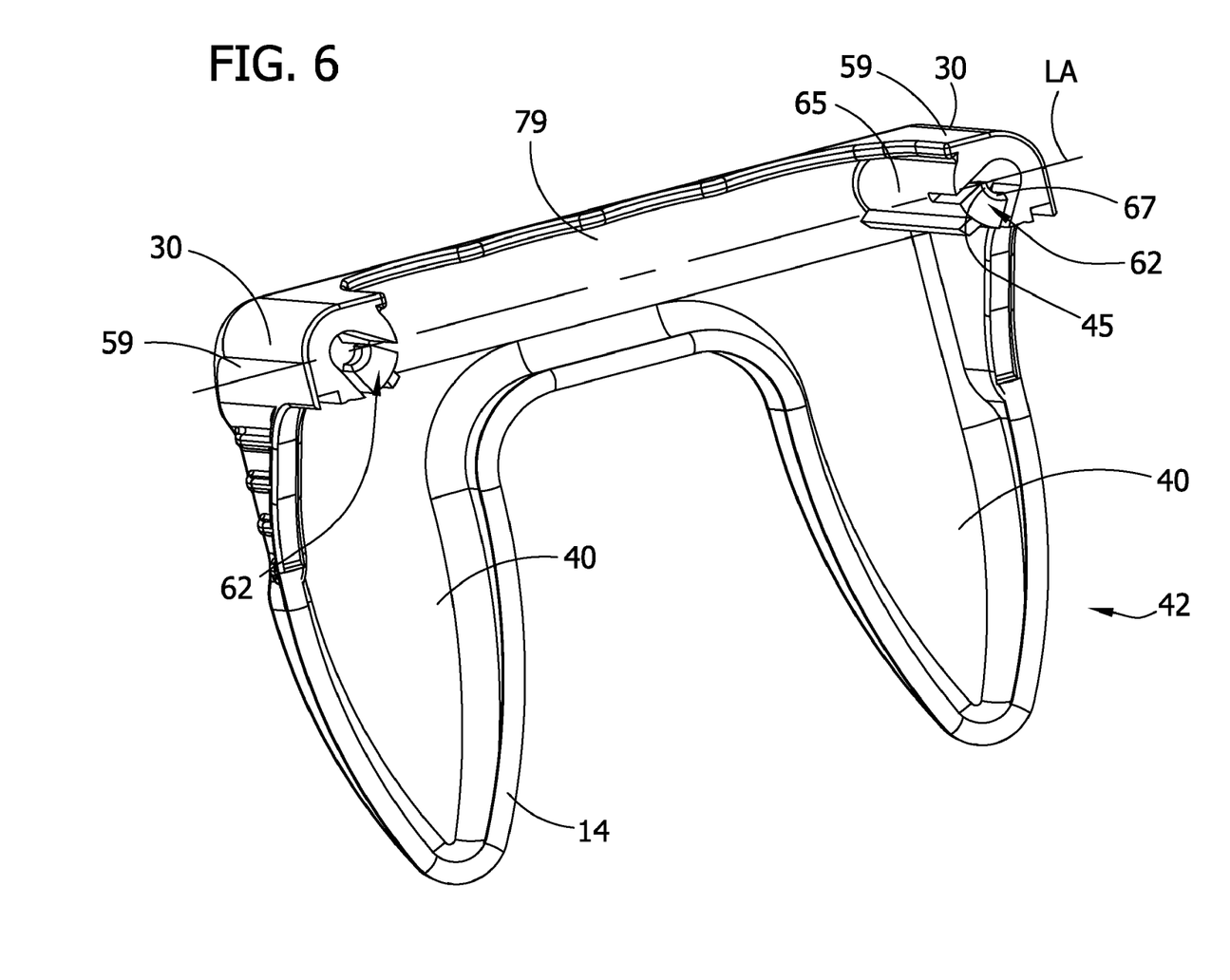
FIG. 6 is a rear perspective of the positioning member of the clamp of FIG. 1.

Referring to FIG. 6, each positioning member 30 includes a finger, generally indicated at 62, which is flexibly joined with the remainder of the positioning member at its base 65. The positioning tab 45 is located at the free end margin 67 of the finger 62. While the positioning tab 45 is located at the end of the receptacle 21 remote from the clamping member 42, it should be appreciated that the positioning tab may be generally located anywhere along the length of the anchor member 30. In response to a sufficiently large force being applied along the axis of the anchor rod 5, the fingers 62 deflect at the bases 65 to move the positioning tabs 45 out of the grooves 33 to adjust the position of the clamping member 42, as previously described.

Figure 7:
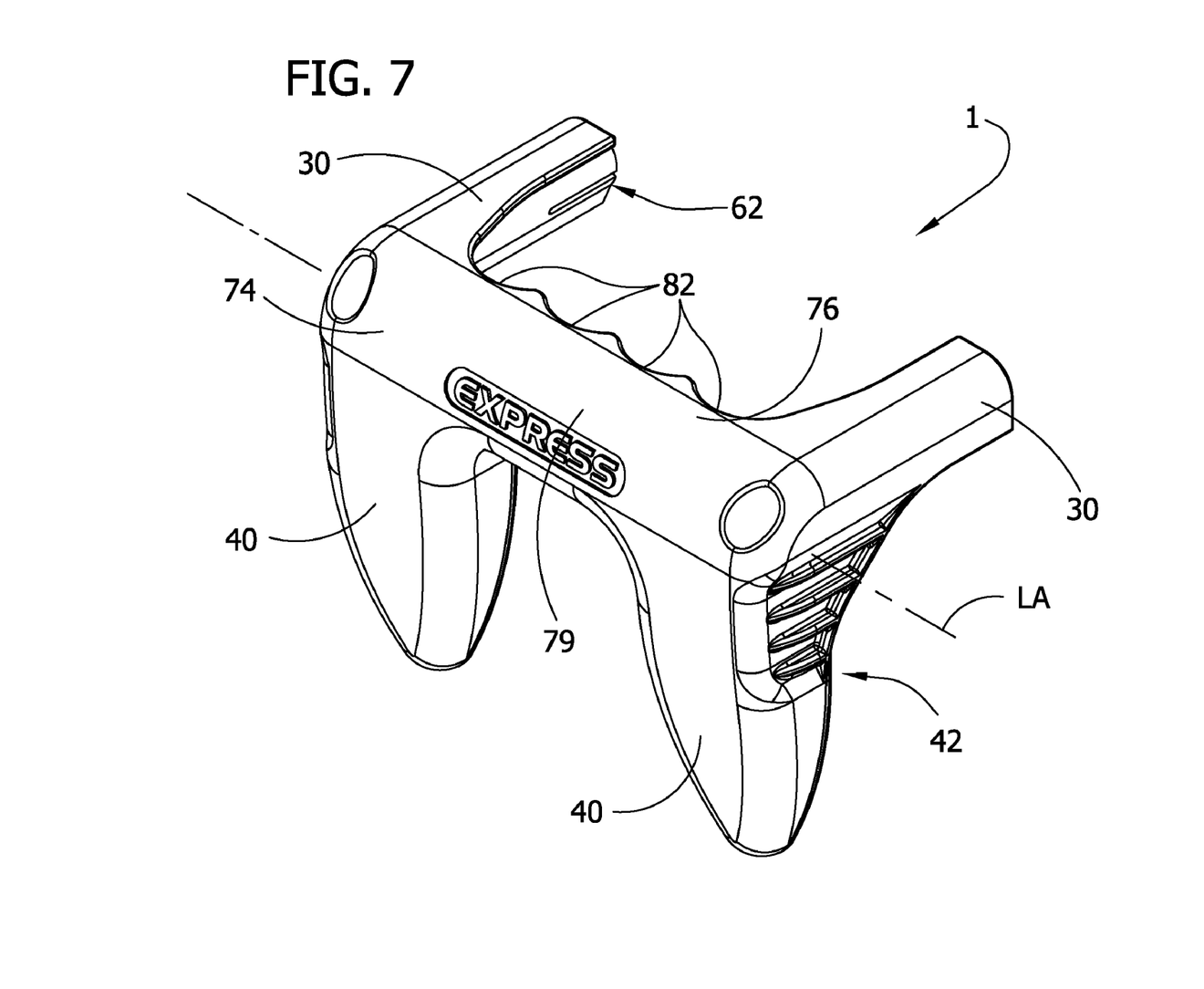
FIG. 7 is a front perspective of the positioning member of FIG. 1.

Referring to FIGS. 6 and 7, a grip member 79 sized and shaped for being gripped in the hand is attached to the pair of positioning members 30 and the legs 40 to assist in gripping the clamp 1 to hold the clamp and reposition the legs 40 relative to the controller 9. As the legs 40 extend outwardly from the grip member 79 and positioning members 30, the legs and grip member generally form a "U" shape that allows the grip member to be gripped by a hand. The grip member 79 may be molded of plastic and, optionally, a resin that is chemically compatible with disinfectants and cleansers used in a hospital setting such as XENOY.

The grip member 79 has a longitudinal axis LA and a curved contour which is curved in a direction about the longitudinal axis. The legs 40 taper in width toward an end which is remote from the grip member 79. The grip member 79 has a front 74 and a back 76. The back 76 of the grip member 79 forms a plurality of finger wells 82 to receive portions of the fingers of the hand.

Figure 8:
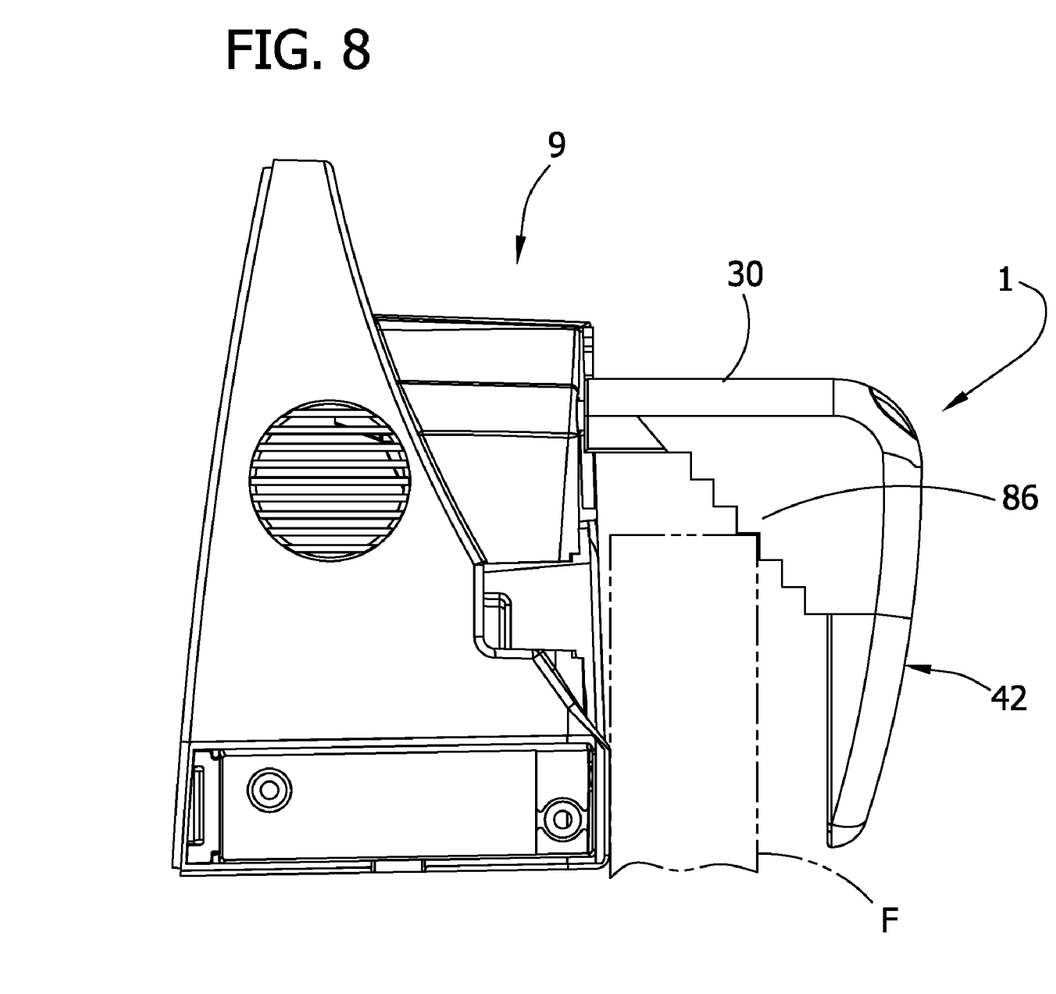
FIG. 8 is a side elevation of a controller of a sequential compression device and another embodiment of the clamp.

Referring to FIG. 8, another embodiment of the clamp 1 includes a stepped formation 86 that extends between each anchor member 30 to the clamping member 42. The stepped formation 86 contacts the support and allows the controller 9 and clamp 1 to be secured so that the controller is held level and allows for a tighter fit between the clamp 1 and support such as a footboard F shown in phantom.

Figure 9:
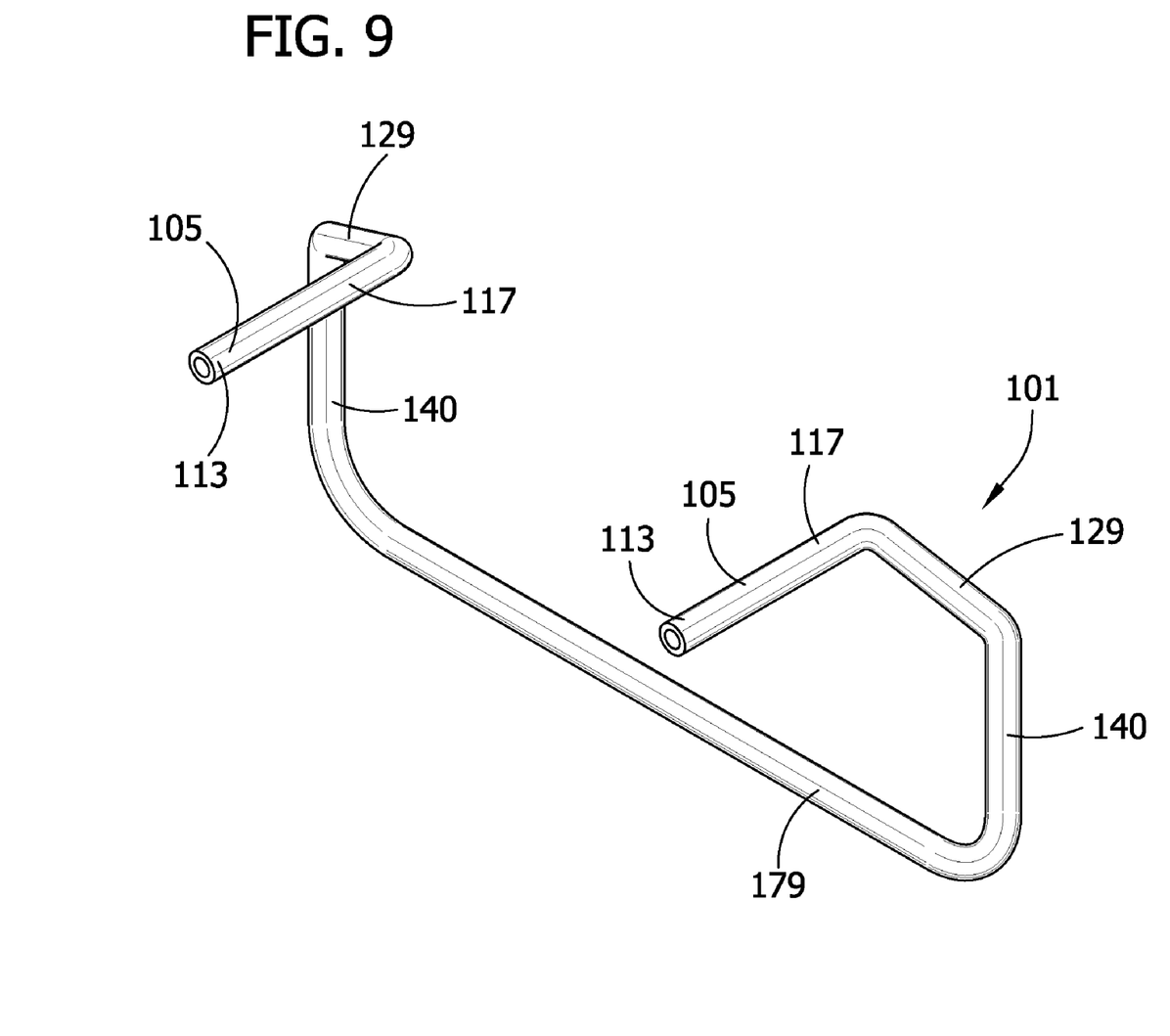
FIG. 9 is a rear perspective of still another embodiment of the clamp.
Figure 10:
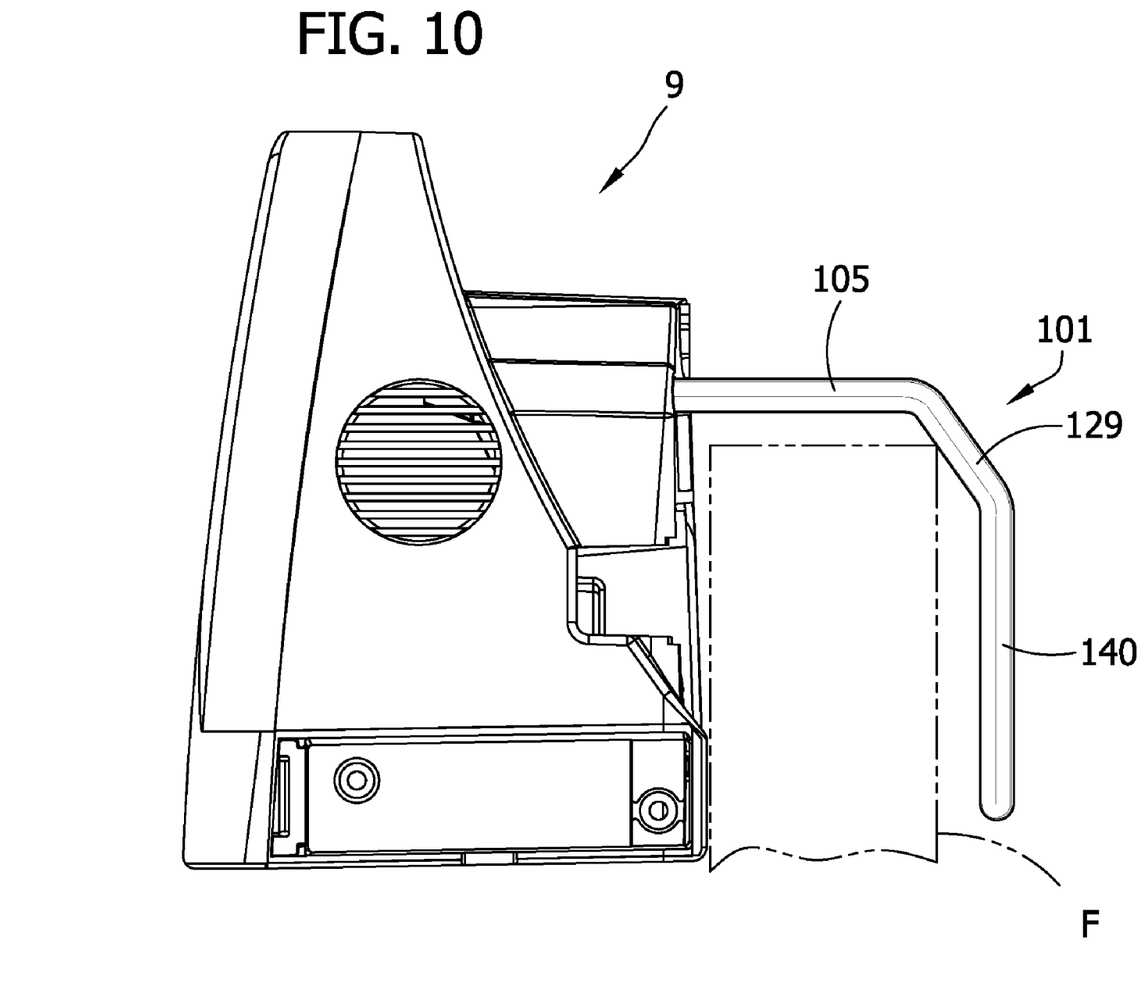
FIG. 10 is a side elevation of a controller of a sequential compression device incorporating the clamp of FIG. 9.
Figure 11:
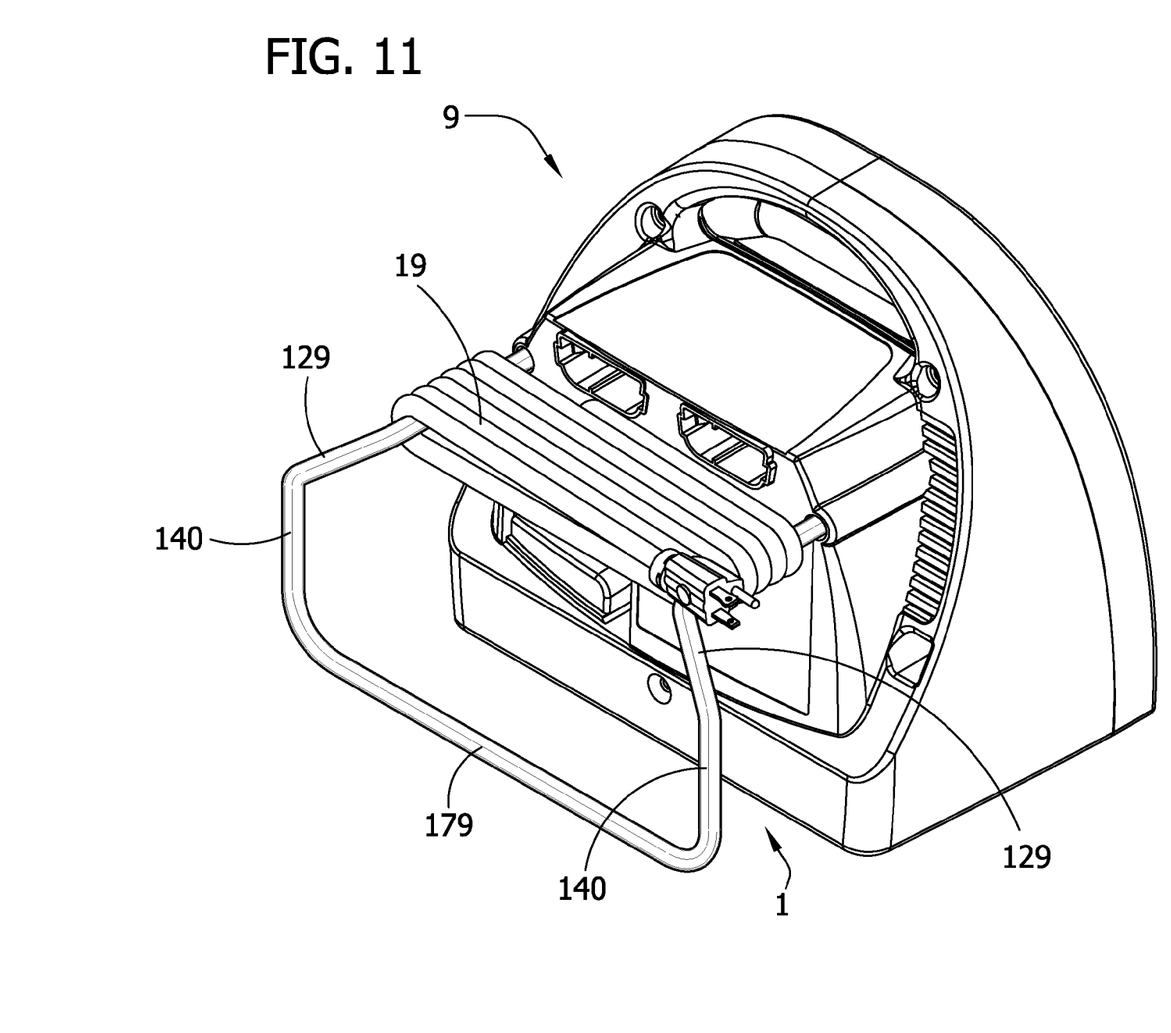
FIG. 11 is a rear perspective of the controller and clamp shown in FIG. 10 with the power cord wrapped around the clamp for storage of the controller and clamp.

FIGS. 9-11 illustrate another embodiment of a clamp 101 for securing an object to a support and, for example, a footboard F (FIG. 10). Parts of the clamp 101 corresponding to those of the clamp 1 are given the same reference numeral, plus "100." The clamp 101 includes a pair of anchor rods 105, each defining a longitudinal axis. The first end portion 113 of each rod 105 may be affixed to the controller body 25 in a suitable manner such as by bolts (not shown) threaded into the opening at each first end portion 113. A clamp (not shown) may be formed as one piece with the controller body 25. Each anchor rod 105 includes a second end portion 117.

The clamp 101 includes a pair of extension members 129 that extend outward and downward from the longitudinal axes of the anchor rods 105. A pair of legs 140 project downward from the extension members 129. A crosspiece 179 is attached to the pair of legs 140 and is suitable for gripping the clamp 101. In the embodiment of FIGS. 9-11, the anchor rod 105, extension members 129 and crosspiece 179 form a hook to attach the controller 9 to the support structure, such as the foot board F shown in FIG. 10. The anchor rods 105, extension members 129, legs 140 and crosspiece 179 may be affixed by a variety of methods. Preferably and in the illustrated embodiment, the anchor rods 105, extension members 129, legs 140 and crosspiece 179 are formed as one piece with each other. The anchor rods 105, extension members 129, legs 140, and crosspiece 179 may be constructed of plastic or metal and, preferably, are constructed of stainless steel.

The controller 9 includes a power cord 19 for providing electrical power to the controller (FIG. 11). The power cord 19 may be wrapped around the anchor rods 105 of the clamp 101 by a practician when the controller 9 is not in use. This allows the controller 9 to be compactly stored in the hospital setting. The extension members 129 extend outward from the longitudinal axis of the anchor rods 105 such that the wrapped power cord becomes secured between the controller 9 and the extension rods 129. This arrangement prevents the wrapped power cord from becoming a trip hazard by sliding off the clamp and unwrapping.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above methods without departing from the scope of the invention, it is intended that all matter contained in the above description and shown in the accompanying figures shall be interpreted as illustrative and not in a limiting sense.

What is claimed is:

1. A telescopingly adjustable clamp for securing an object to a support, the clamp comprising:
   an anchor rod having a first end portion, a second end portion and a longitudinal axis, the anchor rod being adapted for affixation to the object at the first end portion of the anchor rod and including a plurality of axially spaced, circumferentially extending grooves formed in the anchor rod, the grooves defining at least one barrier wall between adjacent grooves;
   a positioning member defining a receptacle sized and shaped to receive at least the second end portion of the anchor rod and to allow motion of the anchor rod relative to the positioning member in the receptacle, the positioning member comprising a positioning tab projecting into the receptacle and sized and shaped to be received in one of the grooves and retained in said one groove by the barrier wall;
   at least one of the positioning tab and the barrier wall being resiliently deflectable upon application of a release force along the longitudinal axis of the anchor rod for moving the positioning tab out of one of the grooves;
   a clamping member supported by the positioning member and extending generally radially outwardly from the longitudinal axis of the anchor rod, wherein relative movement of the anchor rod and the positioning member changes the distance between the clamping member and the first end portion of the anchor rod for clamping the object to the support;
   wherein the receptacle includes a capture section in which a second end of the anchor rod is captured, and wherein the capture section of the receptacle has a larger diameter than a support section of the receptacle, and wherein the anchor rod has a retainer projecting outwardly from the anchor rod to a radius that is larger than that of the support section.

2. The telescopingly adjustable clamp as set forth in claim 1 wherein the positioning tab is located at an end of the receptacle remote from the clamping member, and wherein the positioning member includes a finger having a base flexibly joined with the remainder of the positioning member and a free end margin opposite the base, the positioning tab being located generally at the free end margin of the finger.

3. The telescopingly adjustable clamp as set forth in claim 2 wherein the finger defines a portion of the receptacle in the positioning member.

4. The telescopingly adjustable clamp as set forth in claim 2 wherein the support section of the receptacle is sized for sliding but close contacting engagement with the anchor rod on both sides of at least one of the grooves for supporting the anchor rod against lateral movement relative to the positioning member.

5. The telescopingly adjustable clamp as set forth in claim 1 wherein the receptacle includes only a single positioning tab.

6. The telescopingly adjustable clamp as set forth in claim 1 wherein the clamping member includes at least one strip of frictionalizing material for gripping the support.

7. The telescopingly adjustable clamp as set forth in claim 1 wherein the anchor rod constitutes a first anchor rod and the positioning member constitutes a first positioning member, and wherein the telescopingly adjustable clamp further comprises:
   a second anchor rod having a first end portion, a second end portion and a longitudinal axis, the second anchor rod being adapted for affixation to the object at the first end portion of the second anchor rod and including a plurality of axially spaced, circumferentially extending grooves formed in the second anchor rod, the grooves defining at least one barrier wall between adjacent grooves;
   a second positioning member defining a receptacle sized and shaped to receive at least the second end portion of the second anchor rod and to allow motion of the second anchor rod relative to the second positioning member in the receptacle, the second positioning member comprising a positioning tab sized and shaped to be received in one of the grooves and retained in said one groove by the barrier wall;

at least one of the positioning tab of the second positioning member and the barrier wall of the second anchor rod being resiliently deflectable upon application of a release force along the longitudinal axis of the second anchor rod for moving the positioning tab out of one of the grooves;

the clamping member being supported by the first and second positioning members.

8. The telescopingly adjustable clamp as set forth in claim 7 further comprising a grip member attached to the two positioning members for gripping the clamp during application or removal of the clamp from the support and wherein the clamping member comprises two spaced apart legs projecting generally radially from the longitudinal axis of the first and second anchor rods, respectively.

9. The telescopingly adjustable clamp as set forth in claim 1 further comprising a stepped formation extending between the clamping member and the positioning member for engaging the support.

10. The telescopingly adjustable clamp as set forth in claim 1 in combination with the object, and wherein the object is a medical device, the anchor rod being connected to the medical device and the clamping member being arranged in opposed relation to the medical device for clamping the support between the medical device and the clamping member.

11. The telescopingly adjustable clamp and object as set forth in claim 10 wherein the object is a controller for a sequential compression device.

12. The telescopingly adjustable clamp as set forth in claim 1 wherein the second end portion of the anchor rod is free of structure in opposed relation to the clamping member.

13. The telescopingly adjustable clamp as set forth in claim 1 wherein the second end portion of the anchor rod is located in the receptacle of the positioning member.

* * * * *